US008288617B2

United States Patent
Johnson et al.

(10) Patent No.: US 8,288,617 B2
(45) Date of Patent: *Oct. 16, 2012

(54) SQUASH WITH IMPROVED DISEASE RESISTANCE

(75) Inventors: William C Johnson, Sacramento, CA (US); John Kao, Davis, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 1018 days.

This patent is subject to a terminal disclaimer.

(21) Appl. No.: 12/197,908

(22) Filed: Aug. 25, 2008

(65) Prior Publication Data

US 2008/0320614 A1 Dec. 25, 2008

Related U.S. Application Data

(63) Continuation of application No. 11/221,998, filed on Sep. 7, 2005, now Pat. No. 7,432,420.

(51) Int. Cl.
- *A01H 5/00* (2006.01)
- *A01H 5/10* (2006.01)
- *A01H 5/08* (2006.01)
- *C12N 5/04* (2006.01)

(52) U.S. Cl. ........ 800/310; 800/265; 800/298; 800/295; 800/301; 435/419

(58) Field of Classification Search .................. None
See application file for complete search history.

(56) References Cited

U.S. PATENT DOCUMENTS

| 6,133,505 A | 10/2000 | Gronenborn |
| 2003/0167540 A1 | 9/2003 | Superak et al. |
| 2004/0205843 A1 | 10/2004 | Hanley-Bowdoin et al. |

OTHER PUBLICATIONS

Bernacchi et al (Theor Appl Genet (1998) 97:381-397.*
Gaba et al., "Invited Review: Cucurbit Biotechnology—the Importance of Virus Resistance", *In Vitro Cell. Dev. Biol.—Plant*, 40:346-358 (2004), herewith.
Herrington et al.,"'Dulong QHI' and 'Redlands Trailblazer', PRSV-W-, ZYMV-, and WMV-resistant Winter Squash Cultivars", *HortScience*, 36(4):811-812 (2001), in U.S. Appl. No. 11/221,998.
International Search Report for International Application No. PCT/US2006/033570 (International Publication No. WO 2007/030356), mailed Jun. 12, 2007, in U.S. Appl. No. 11/221,998.
Lebeda et al., "Resistance in *Cucurbita pepo* and *Cucurbita maxima* germplasms to cucumber mosaic virus", *Genetic Resources and Crop Evolution*, 43:461-469 (1996), in U.S. Appl. No. 11/221,998.
McCreight et al., "Reaction of *Cucurbit* Species to Squash Leaf Curl Virus and Sweetpotato Whitefly", *J. Amer. Soc. Hort. Sci.*, 116(1):137-141 (1991), in U.S. Appl. No. 11/221,998.

* cited by examiner

*Primary Examiner* — Medina A Ibrahim
(74) *Attorney, Agent, or Firm* — Alissa M. Eagle; Arnold & Porter LLP

(57) ABSTRACT

A squash plant having high level geminivirus resistance and a method for developing a squash plant having high resistance to geminvirus.

13 Claims, No Drawings

SQUASH WITH IMPROVED DISEASE RESISTANCE

CROSS-REFERENCE TO RELATED APPLICATIONS

This application is a continuation of U.S. patent application Ser. No. 11/221,998 filed on Sep. 7, 2005, now U.S. Pat. No. 7,432,420, which application is hereby incorporated by reference.

BACKGROUND OF THE INVENTION

1. Field of the Invention

The field of the invention is plant breeding, and, in particular, the development of squash plants having high resistance to geminiviruses, such as Squash leaf curl virus (SLCV). The invention also pertains to squash plants having high resistance to geminiviruses as well as resistance to potyviruses, such as Zucchini yellow mosaic virus (ZYMV), Watermelon mosaic virus 2 (WMV-2), and Papaya ringspot virus (PRSV).

2. Description of Related Art

Squash is the common name for a collection of plants that produce edible seeds, fruits and flowers. Squashes are divided into two general groups, summer and winter. Fruits from the summer group are harvested and consumed at an immature state. Winter squash (which includes market classes sometimes called pumpkin) fruits are harvested at maturity, after the fruits have ripened and developed a hard rind.

Winter squashes are the mature fruits of three Cucurbit species: *Cucurbita maxima, Cucurbita moschata* and *Cucurbita pepo*. Fruit from winter squash varieties are grown to physiological maturity and typically stored for consumption during the winter months or used for ornamental purposes. Examples of common winter squashes are acorn, butternut, hubbard, and spaghetti squash, as well as the Halloween type pumpkins.

Most summer squash varieties are *Cucurbita pepo*, and their fruits are typically harvested and consumed at an immature stage. The flowers of summer squash can also be harvested for consumption. There are many types of summer squash, including yellow crookneck, yellow straightneck, scallop, Lebanese, and green and gray zucchini. Green zucchini is the type of *C. pepo* squash preferred by consumers in Europe and many parts of the North America, as well as in other regions. Unlike winter squashes, summer squash fruit have a short shelf life, and are typically consumed within days of harvest. Because of the extended ability to ship produce over long distances there are some markets where the terms "summer" and "winter" squash no longer reflect a restriction on availability and all types can be found in these markets year round.

All squash are indigenous to North and South America, and the *Cucurbita pepo* varieties are most likely domesticated from the wild *Cucurbita texana* and *Cucurbita fraterna* species (Sauer (1993) Historical geography of crop plants—a select roster. CRC Press, Boca Raton, Fla.). Squash, along with beans and maize, were the primary agricultural crops of Native North Americans for at least 300 years before the arrival of the Europeans. These crops were grown in an intercropping system. Because of their importance in the culture, the crops were coined 'The Three Sisters' in the Iroquois tribe's creation myth (Erney, Diana. 1996. Long live the Three Sisters. Organic Gardening. November. p. 37-40).

After introduction to Europe by explorers in the 1500's, squash spread as an agricultural crop around the world. Summer squash varieties show considerable diversity, and are classified commercially into market types by their biological species, fruit shape, and fruit coloring. The green zucchini, white scallop and yellow crookneck types are some examples of diversity found in *Cucurbita pepo*.

Many pathogens infect squash, though studies have shown that viral diseases cause the most severe damage. For many years, four viral pathogens have presented the main challenge to squash production in almost every growing region in the world. Of these four most common viral pathogens, three belong to the Potyvirus genus. These are ZYMV, WMV-2 and PRSV. Potyvirus virions contain one or two linear, positive-sense single stranded RNA(s). Viruses in this genus have a genome between 8,500 and 10,000 nucleotides.

The International Committee on Taxonomy of Viruses (ICTV) operates under the auspices of the Virology Division of the International Union of Microbiological Societies. In the universal scheme developed by the ICTV, virion characteristics are considered and weighted as criteria for making divisions into families, in some cases subfamilies, and genera. The ICTV database is similar in structure to the Dewey Decimal Classification System. The ICTV virus code for PRSV is 00.057.0.01.045. For ZYMV, the ICTV code is 00.057.0.01.077. The ICTV virus code for WMV-2 is 00.057.0.01.073.

The fourth traditional viral pathogen of squash is Cucumber mosaic virus (CMV), a cucumovirus. Cucumoviruses belong to the family Bromoviridae (ICTV Virus Code: 00.010.0.04.001).

There are serological and molecular diagnostic tests to diagnose which of these traditional viral pathogens have infected squash plants, as it is difficult to visually distinguish viral symptoms caused by any one of these viruses.

The visual diagnosis of virus infection can be even more difficult in growing areas where infection by more than one virus is commonplace. Common foliar symptoms caused by these traditional pathogens are plant stunting due to shortening of the internodes and an overall reduced growth rate. Foliar symptoms can include mottling, puckering, curling and distortion of the leaves; mosaic patterns are also common and range in color from green to yellow. Generally, the younger the plant at the time of infection, the more pronounced the symptoms.

In addition to these foliar symptoms, fruit defects have been described as being warty, bumpy and deformed in shape. These defects typically make the fruits unmarketable (Bernhardt et al. Cucumber Disease: A Practical Guide for Seedsmen, Growers and Agricultural Advisors, Petoseed Company. 1988; Zitter et al. Compendium of Cucurbit Diseases, American Phytopathological Society, 1996). Many plant viruses can be mechanically transmitted, but by far the most common mode of transmission of these four viruses is by aphids in a non-persistent manner. Aphids feed on plant sap, and acquire the nutrients therein through a specialized feeding tube designed both for probing leaves and for siphoning off the sap. If an aphid feeds on an infected plant, the virus particles stay in their mouthparts. When the insect then feeds on an uninfected plant, the virus particles are transmitted to the new host as the aphid probes again for its food. It takes only a few seconds for virus transmission to occur.

Both commercial or volunteer crops, and weeds, can harbor squash infecting viruses and serve as sources for additional infection. Some viruses that infect squash, such as CMV, have a very broad host range. CMV is an aphid-transmitted virus with worldwide distributions that can infect up to 800 plant species. Other viruses, such as SLCV (ICTV virus code is 00.029.0.03.035), infect a much more limited but diverse (beans and squash) group of plants. SLCV is transmitted persistently by the sweet potato whitefly, *Bemisia tabaci*, not by aphids. Removing weeds or volunteers, or growing the commercial crop away from these other potential hosts or when the insect vectors are not plentiful can help reduce the incidence of viral diseases.

Once the virus has been identified, a control strategy that includes insect suppression or eradication, sanitation, crop rotation, and planting schedules can be developed. The diversity of insect vectors makes controlling viruses by controlling the vector difficult, especially if conditions are conducive for vector proliferation. In some cases, the extent of virus infection can be limited by controlling the vector. Weather and crop timing can be of great influence on insect vector populations and the subsequent amount of virus that develops. In arid and semi-arid growing regions, aphids proliferate in the spring and early summer when temperatures are generally below 90-95° F., but their numbers dramatically fall when temperatures exceed 95° F. In contrast, whiteflies develop and increase in number quickly at temperatures in excess of 90-95° F. Therefore, viruses that are associated with each of these vectors also will be most common during the respective weather conditions. Crops that are planted late in the growing season are often at highest risk because insect vector populations and virus levels may have built up on earlier crops.

Insecticide or mineral oil sprays can be used for controlling insect vectors. Good results have been reported using a combination of Platinum™, a soil-applied insecticide that provides control of aphids and whiteflies, and Fulfill™, a foliar applied insecticide that suppresses whitefly populations and stops aphid feeding within 1-2 hours of initial ingestion, to reduce the transmission of viruses. Platinum™ contains the active ingredient thiamethoxam. Its effectiveness is a function of its systemic properties; because of its high water solubility, moderate soil absorption and low the partition coefficient of thiamethoxam, it moves quickly through the plant to provide protection.

Fulfill™ is a selective, foliar aphicide with a unique mode of action that is not harmful to some beneficial insects. Fulfill™ also has some limited activity against whiteflies in vegetable crops. The active ingredient in Fulfill™ is pymetrozine.

Additional to chemical control methods, growers can use several other horticultural practices to reduce virus-induced damage. One of these is known as mid-bedding, where seed is planted in V-shaped trenches between plant beds in the early spring, and the trenches are covered with plastic. The main benefit is increased soil temperatures to hasten plant development for early production, but a side benefit is a possible reduction in early aphid populations and associated viruses on the young plants. Reflective mulches, which are intended to disorient aphids, have been used with varying degrees of success for limiting aphid-transmitted viruses. For the viruses that are transmitted mechanically as well as by insects, cultivation and other equipment should be cleaned and disinfected prior to being moved from infected to non-infected fields.

While chemical and other controls can sometimes be somewhat helpful in curtailing virus-induced diseases, alternative and better control strategies are clearly needed. Chemical control methods are a particular concern. Their efficacy can be a problem, first of all, as insects can escape the spray.

Of greater concern is the fact that whiteflies develop resistance to a pesticide when used frequently. In tomato, pesticide resistant whiteflies of *B. tabaci* have developed that can vector over 20 different tomato-infecting begomoviruses. If resistance to the pesticide develops, the mechanism to limit the virus spread is lost to all viruses transmitted by that vector (Morales, F. J., P. K Anderson: The emergence and dissemination of whitefly-transmitted geminiviruses in Latin America, Archives of Virology, Volume 146, Issue 3, March 2001, Pages 415-441; Polston, J. E., P. K. Anderson (1997): The emergence of whitefly transmitted geminiviruses in tomato in the western hemisphere, Plant Disease 81:1358-1369; Zeidan, M., et al., 1999: Molecular analysis of whitefly-transmitted tomato geminiviruses from Southeast and East Asia, Trop. Agric. Res. Ext. 1, 107-115.). Further, there are increasing pressures from regulatory agencies to withdraw approvals for pesticide use, and from environmental and consumer advocates, who have concerns about the environmental consequences of pesticide use and about the effect these pesticides may have on human health. Therefore, there is a long-standing need in commerce for alternate strategies to control these viral diseases.

In recent years, squash varieties having some level of resistance to certain plant viruses have been developed. Examples include the varieties Noche and Contender (Rogers), which are dark green zucchini varieties with reported resistance to ZYMV and WMV-2. Resistant varieties can be incorporated into a virus control strategy but are generally only resistant to specifically designated viruses, and not broadly resistant to the complete assortment of squash infecting viruses.

Seminis has created and obtained regulatory approval in the United States to sell multiple virus resistance transgenic squash. One transformation event is referred to as ZW-20. A second event, called CZW-3, confers resistance to ZYMV, WMV-2 and CMV. Both transformation events express the viral coat protein genes that were inserted into the plant DNA using *Agrobacterium* mediated transformation. Varieties containing the ZW-20 event have resistance to ZYMV and WMV-2; those containing the CZW-3 event are also resistant to CMV.

Except for the virus resistance phenotype, the transgenic lines look and behave the same way as their non-transgenic counterparts. Seminis markets a number of varieties that contain these transgenic events, including the varieties 'Declaration II' (green zucchini), 'Independence II' (green zucchini), 'Patriot II' (yellow straightneck), 'Destiny III' (yellow crookneck), 'Liberator III' (yellow straightneck), 'Justice III' (green zucchini), 'XPT 1832 III' (yellow straightneck), and 'Judgement III' (green zucchini). In addition, one transgenic variety called 'Conqueror III' contains non-transgenic intermediate resistance to PRSV. The addition of 'II' or 'III' to the variety name refers to the transformation event, respectively ZW-20 and CZW-3.

Varieties which are well matched to their target growing regions, such as Conqueror III targeted to the South-eastern USA, will have resistance to all the viral diseases likely to be encountered in that region. Similarly Justice III and Judgement III (green zucchini varieties) and XPT 1832 (yellow precocious straightneck) have high resistance to the three viruses likely to be encountered in the Northeastern and Midwestern USA (CMV, WMV-2, ZYMV).

Unlike some of the well-established common viral diseases described above, SLCV is the causative agent of a relatively new squash disease called squash leaf curl. SLCV is a geminivirus belonging to the genus *Begomovirus*. Geminiviruses are plant viruses that belong to the family Geminiviridae, first described by Goodman in 1977 (Goodman, 1977a, 1977b). Geminiviruses are characterized by the unique twin shape of a fused icosahedral viral particle. The geminate virions contain a circular single-stranded DNA (ssDNA) genome. The family Geminiviridae is comprised of three genera, all of which share similarities in genome organization, insect transmission, and host range.

The genus *Begomovirus* consists of viruses with monopartite and bipartite genomes. Begomoviruses are transmitted by whiteflies in a persistent, circulative, non-propagative manner, and infect dicotyledonous plants. There is agreement that plant pathogenic Begomoviruses have a complex association with the whitefly, their insect vector, though aspects concerning viral genetic activity (genome replication and gene transcription) within the insect remain controversial.

During the past 25 years geminiviruses have become a particular problem on squash in dry regions where the whitefly vectors are present in large numbers. There are now three *begomoviruses* identified in squash and it is expected that this number will grow. The current list includes Squash mild leaf curl virus (SMLCV) from California, SLCV from the United States (Arizona, California, and Texas), Mexico (Sinaloa and Sonora), Guatemala, Nicaragua and Panama, and Cucurbit leaf curl (crumple) virus (CuLCV) from the USA (Arizona, California, and Texas) and Northern Mexico (Coahuila). Most of these begomoviruses are capable of forming viable recombinants with related viruses in the squash leaf curl virus group. This ability to recombine is thought to expand diversity within the virus group, and can explain why these geminivirus-induced diseases have spread so quickly. In addition to the pathogens' rapid evolution, the development of irrigation in arid and semi-arid growing regions has led to a longer growing season, and to increases in host plant densities. These in turn, have resulted in increased whitefly populations and the proliferation of begomoviruses.

SLCV is a typical example of the viruses in this group. SLCV has geminate particles, 22×38 nm in size (Cohen, S.; Duffus, J. E.; Liu, H. Y. (1989) Acquisition, interference, and retention of cucurbit leaf curl viruses in whiteflies. Phytopathology 79, 109-113), and the virus is associated with maturing phloem sieve tube elements (Hoefert, L. L. (1987), Association of squash leaf curl virus with nuclei of squash vascular cells. Phytopathology 77, 1596-1600). SLCV was first identified in the late 1970's and was originally transmitted by *Bemisia tabaci* biotype A whitefly, but became a more severe problem in the late 1980's when it became transmissible by biotype B. In addition to vectoring SLCV, extensive feeding of the *Bemisia tabaci*, biotype B whitefly on squash causes a leaf silvering disease. The combination of SLCV and silvering disease can be devastating. SLCV causes severe losses of squash, melons and related cucurbits in Arizona and California (USA) (Duffus, J. E.; Flock, R. A. (1982) Whitefly-transmitted disease complex of the desert southwest. California Agriculture 36, 4-6; Nameth, S. T.; Laemmlen, F. F.; Dodds, J. A. (1985) Viruses cause heavy melon losses in desert valleys. California Agriculture 39, 28-29). Typical symptoms of SLCV include a bright yellow mottling or mosaic of the leaves, which are accompanied by pronounced upward leaf curling and enations on the underside of leaves. Infected squash plants are stunted and normally do not produce additional foliage after infection, and fruit set will be greatly reduced. Fruit on infected plants may become misshapen and discolored. Plants may be killed when the disease is severe, especially if infection occurs early during the plant's development.

Silvering disease is described in Yokomi, R. K., K. A. Hoelmer, and L. S. Osborne. 1990. Relationships between the sweet potato whitefly and the squash silverleaf disorder. Phytopath. 80:895-900. (Also Schuster, K. J., J. B. Kring, and J. F. Price. 1991. Association of the sweet potato whitefly with a silverleaf disorder of squash. HortSci. 26:155-156; Costa, H, S., D. E. Ullman, M. W. Johnson, and B. E. Tabashnik. 1993. Squash silverleaf symptoms induced by immature, but not adult, *Bemisia tabaci*. Phytopath. 83:763-766; Jimenez, D. R., J. P. Shapiro, and R. K. Yokomi. 1993. Biotype-specific expression of dsRNA in the sweet potato whitefly. Entomol. Exp. Appl. 70: 143-152). Silvering disease is seen on cucurbits infested by *Bemisia tabaci* B-type, but is not necessarily associated with SLCV. It has been suggested that silvering disease could be due to infection by another virus (Bharathan, N.; Narayanan, K. R.; McMillan, R. T. 1992. Characteristics of sweet potato whitefly-mediated silverleaf syndrome and associated double-stranded RNA in squash. Phytopathology 82, 136-141), but it is now generally thought to be induced physiologically by the feeding of the B-type (hence its proposed name *B. argentifolii*) whitefly (Perring, T. M., Cooper, A. D., Rodriguez, R. J., Farrar, C. A., and Bellows, T. S. 1993. Identification of a whitefly species by genomic and behavioral studies. Science 259:74-77 and Brown, J. K., Frohlich, D. R., and Rosell, R. C. 1995. The sweet potato or silverleaf whiteflies: Biotypes of *Bemisia tabaci* or a species complex? Ann. Rev. Entomol. 40: 511-534).

SLCV was first reported in California damaging crops of *Cucurbita pepo*. The SLCV group evolves rapidly (Brown J. K., A. M. Idris, C. Alteri and D. C. Stenger (2002) Phytopath. 92:734-742). This has created some concern over the potential emergence of a new cucurbit-infecting begomovirus species capable of forming viable recombinants with related viruses in the squash leaf curl virus cluster.

Control of SLCV mainly aims at eliminating or excluding the vector *Bemisia tabaci*. Endosulfan and other insecticides have been used in an attempt to reduce whitefly density. Protecting rows of seedlings with spun-bonded polyester as a floating cover was found more effective than any other mechanism to date (Natwick, E. T.; Durazo, A. (1985) Polyester covers protect vegetables from whiteflies and virus diseases. California Agriculture 39, 21-22.). This is an extreme and expensive measure to take for a field crop, as the cloth must be lifted to ensure pollination. In many growing areas, the additional material cost (cloth) and labor is prohibitively expensive, and can be ineffective in windy environments. Transmission of SLCV by mechanical means has not been documented.

While some level of resistance in *Cucurbita* spp. to SLCV was reported in 1984 (McCreight, J. D. (1984) Tolerance of *Cucurbita* spp. to squash leaf curl. Report, Cucurbit Genetics Cooperative, USA No. 7, 71-72), to date no resistance or high resistance to SLCV has been reported in any commercial squash varieties (*C. pepo*).

SUMMARY OF THE INVENTION

The invention provides a squash plant having high resistance to geminivirus. The geminivirus may be any geminivirus affecting squash plants, such as Squash leaf curl virus (SLCV). The geminivirus resistance may be derived from the squash line designated as Entry 1, which shows intermediate resistance to SLCV.

The squash plant preferably also has potyvirus resistance, such as the potyvirus resistance found line ZGN 47-5012. The characteristics of this line are described in greater detail below.

The squash plant may be transformed by one or more genetic elements, or it may be non-transgenic.

Squash plants are challenged by virus and individual plants are evaluated and given an SLCV resistance score from 1-5, depending the severity of the reaction, or symptoms. A squash line or variety is highly resistant if it has greater than 75% of the plants in the least symptomatic levels of 1 of 2. Preferred are squash lines or varieties having a level of SLCV resistance in which greater than about 90% of scored plants score a 1 or 2 resistance level to the SLCV test.

The squash plant also preferably has an average geminivirus resistance score of less than about 2.0, and even more preferably less than about 1.8 and more preferably less than about 1.6.

In another aspect of the invention, the squash line has an average geminivirus resistance score at least 0.5 better than the geminivirus resistance score obtained from the line designated Entry 1 when grown under comparable conditions.

A preferred squash plant of the invention produces summer squash having desired characteristics of marketable fruit, such as uniformly dark green fruit, yellow fruit or cylindrical and substantially non-tapering fruit, and combinations of these traits and other desirable characteristics of marketable fruit.

The invention also contemplates a method of producing a squash crop comprising growing a plurality of squash plants having high level geminivirus resistance in a field and harvesting squash from the squash plants. The squash crop harvested according to the method is also contemplated.

The invention further provides seed of a highly SLCV resistant inbred squash plant designated Entry 8 as well as a squash plant sharing the physiological and morphological characteristics of Entry 8, the seed having been deposited with the American Type Culture Collection (ATCC), Manassas, Va. 20110-2209 USA, as ATCC Accession No. PTA-6962.

In another aspect, the invention provides a method for producing squash seed comprising crossing two parent squash plants and harvesting the resultant squash seed, where at least one of the parent squash plants is the squash plant designated Entry 8. The method more preferably comprises the step of growing an F1 squash plant from seed resulting from the cross, crossing the F1 squash plant to another squash plant, and selecting progeny squash plants having desired marketable traits, the progeny having high level geminivirus resistance. In an even more preferred embodiment, the method comprises two or more generations of backcrossing to squash plants, followed by one or more generations of self-fertilization.

The invention also provides seed produced by the method described above, as well as a squash plant, or parts thereof, produced by growing the seed and squash harvested from the squash plant.

In a different aspect, the invention provides protoplasts or regenerable cells obtained from the squash plant having high level geminivirus resistance. Cells or protoplasts may be produced from a plant tissue selected from the group consisting of: leaf, pollen, cotyledon, hypocotyl, embryos, root, fruit, flower, seed, shoot and stem. The invention further provides a squash plant regenerated from tissue culture and having high level geminivirus resistance. The plant or parts thereof may have been transformed to contain one or more transgenes.

The invention also provides a cutting produced from the squash plant having high level geminivirus resistance, including a rootstock or scion.

In a different embodiment, the invention provides a method for developing a squash plant that has high resistance to SLCV, the method comprising the steps of: a) crossing a first squash line having resistance to SLCV with a second squash line having resistance to potyvirus; and b) performing one or more selection and crossing steps to develop a squash line having high resistance to SLCV. The method may comprise two or more selection and crossing steps, including selection for potyvirus resistance. In one preferred embodiment the first squash cultivar is Entry 1. In a separate preferred embodiment, the second squash plant is ZGN 47-5012.

The invention further provides a squash cultivar having high resistance to SLCV produced by the method. The squash cultivar may be resistant to potyviruses, and preferably produces squash having at least one desired characteristic of marketable fruit.

The first squash cultivar may be the male or female parent.

DETAILED DESCRIPTION OF THE INVENTION

The high level geminivirus resistance in squash is a serendipitous discovery from breeding experiments aimed at incorporating potyvirus resistance into intermediate level geminivirus resistant squash. It has unexpectedly been discovered that heretofore unattainable levels of resistance to geminivirus in squash can be developed in the course of introducing the trait of potyvirus resistance into intermediate resistant geminivirus lines.

High resistant squash is provided in the form of germplasm and also by the disclosed methods for enhancing or boosting the geminivirus resistance level of intermediate resistant geminivirus germplasm by a breeding program using potyvirus resistant squash. The potyvirus resistant germplasm contributes some factor capable of boosting the geminivirus resistance to heretofore unavailable high resistance in squash.

Sergio Garza of the Universidad de Sonora in Hermosillo, Mexico (USON) developed the original donor source of intermediate resistance to geminivirus. The creation of this donor source began with the observation of a local Mexican landrace of *C. moschata* with resistance to geminivirus infection. Through many years of breeding, Mr. Garza developed an open pollinated variety of gray zucchini (*C. pepo*) with intermediate resistance to geminivirus infection. In 1998 USON made this variety available to seed companies with the goal of speeding the introduction of this resistance that would be valuable for local farmers. This line was designated as ZGY 46-2604 at Seminis.

Gray zucchinis are a type of *C. pepo* squash preferred by consumers in Mexico, parts of the Mediterranean Basin, and other areas. The fruit of gray zucchini is typified by a cream to very pale green background skin color, with a coarse netting of a darker green color over the lighter background color. The fruit is shorter and more strongly tapered than the typical green zucchini type. ZGY 46-2604 has a commercially acceptable fruit and plant type for a gray zucchini market, such as Mexico. However, for a green zucchini market the fruit is too light in color, too short, and too tapered. The variety Grey Zucchini from Seminis is an open pollinated variety of gray zucchini, and is the market leading variety of gray zucchini sold worldwide.

The ZGY 46-2604 accession was one of the lines used to create the disclosed high geminivirus resistance lines. Each of Entries 6 through 9, described more fully below, are advanced lines selected from crosses of selections beginning with ZGY 46-2604, as well as a selection which represents a potyvirus resistant line. Entries 6 through 9 represent separate lineages derived from the F1 generation of the same cross, and each shows an unexpected boost or enhancement in the geminivirus resistance level, with high resistance under the greenhouse SLCV test described below.

The goal of plant breeding in general is to develop new, unique and superior varieties and hybrids. The breeder initially selects and crosses two or more parent lines, followed by repeated selection and self-pollination among the progeny, producing many new genetic combinations. The breeder can theoretically generate billions of different genetic combinations via crossing, selfing, and mutations. The breeder has no direct control at the cellular level. Therefore, even if beginning with the same original diverse parental lines, two breeders will never develop the same line.

The complexity of trait inheritance influences the choice of the breeding method. Backcross breeding is used to transfer one or a few favorable genes for a simply inherited trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target areas. The best lines are candidates for new commercial cultivars; those still deficient in a few traits are often used as parents to produce new populations for further selection.

These processes, which lead to the final step of marketing and distribution, can take from ten to 30 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits other confounding plant traits or environmental factors mask the true genotypic value. One method of identifying a superior genotype is to observe its performance relative to other experimental plants and to a widely grown standard cultivar. If a single observation is inconclusive, replicated observations provide a better estimate of its genetic worth.

Each growing season, the plant breeder selects the germplasm to advance to the next generation. This germplasm is grown under unique and different geographical, climatic, and soil conditions and further selections are then made, during and at the end of the growing season. The varieties that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he or she develops, except possibly in a very gross and general fashion. The same breeder cannot produce the same variety twice by using the exact same original parents and the same selection techniques. This unpredictability consequently results in large research expenditures to develop new varieties.

Historically, squash populations were maintained by open pollination, with considerable phenotypic variation for such traits as size, shape, and color. The production of hybrid varieties is increasingly favored, and commercial squash cultivars today are predominantly hybrids. The production of hybrid varieties requires homozygous inbred parental lines. Homozygosity of the inbred, or parental, lines ensures uniformity of the F1 hybrid crops.

The development of squash hybrids in a squash plant breeding program requires, in general, the development of homozygous inbred lines, the crossing of these lines, and the evaluation of the hybrids. Squash plant breeding programs combine the genetic backgrounds from two or more inbred lines or various other germplasm sources into breeding populations from which new inbred lines are developed by selfing and selection of desired phenotypes. Hybrids also can be used as a source of plant breeding material or as source populations from which to develop or derive new squash lines. Plant breeding techniques known in the art and used in a squash plant breeding program include, but are not limited to, recurrent selection, backcrossing, double haploids, pedigree breeding, genetic marker enhanced selection, and transformation. Often a combination of these techniques is used. Thus, inbred lines derived from hybrids can be developed using plant breeding techniques as described above. New inbreds are crossed with other inbred lines and the hybrids from these crosses are evaluated to determine which of those have commercial potential.

Commercial potential for a squash cultivar is largely driven by the yield and quality of the fruit. While the preferred fruit type varies by region and by consumer preference, generally, preferred fruit characteristics of marketable fruit include uniformly dark green or yellow fruit and, for green zucchini types, cylindrical and substantially non-tapering fruit. These fruit characteristics as well as other desirable characteristics of the squash plant are all selected by the breeder.

Backcrossing methods can be used with the present invention to improve or introduce a particular characteristic or set of characteristics into an inbred. The term "backcrossing" as used herein refers to the repeated crossing of a hybrid or it's progeny to squash plants having more desirable characteristics. The parental squash plant which contributes the allele or alleles for the desired characteristic is termed the nonrecurrent, or donor, parent. This terminology refers to the fact that the nonrecurrent parent is used one time in the backcross protocol. The parental squash plant to which the allele or alleles from the nonrecurrent parent are transferred is known as the recurrent parent, as it can be used for several rounds in the backcrossing protocol. In a typical backcross protocol, the original inbred of interest (recurrent parent) is crossed to a second inbred (nonrecurrent parent) that carries the trait or traits of interest to be transferred.

The resulting progeny from this cross, sometimes after multiple generations of self pollination and selection, are then crossed again to the recurrent parent and the process is repeated until a squash plant is obtained wherein most or all of the desired morphological and physiological characteristics of the recurrent parent are recovered, in addition to the one or few transferred traits of the nonrecurrent parent. Depending upon the level of similarity between the parents, four or more backcross generations may be required, with selection for the desired trait, before the progeny will contain essentially all traits of the recurrent parent except for the allele or alleles controlling the desired trait(s). Where molecular markers are available for use during the selection process, the program may potentially be accelerated. After a number of backcross generations, a breeder will be satisfied that except for the trait contributed by the donor parent, the genotype is fixed for the recurrent parental genotype. Because of the recurrent backcrossing scheme, however, the alleles from the donor parent will still be heterozygous. To fix these alleles, the last backcross generation is selfed, followed by selection for homozygosity for the donor parent alleles to give pure breeding progeny for the allele or alleles being transferred.

When the term "inbred", "inbred plant" or "inbred squash" is used in the context of the present invention, this also includes any single gene conversions of that inbred. The term single allele converted plant as used herein refers to those squash plants which are developed by a plant breeding technique called backcrossing wherein essentially all of the desired morphological and physiological characteristics of an inbred are recovered in addition to the single allele transferred into the inbred via the backcrossing technique.

Squash has been transformed by genetic elements, see, C. Gonsalves, HortScience 30, 1295-1297 (1995); D. Tricoli et al., Bio/Technology 13, 1458-1465, (1995). Protoplasts or regenerable cells can be produced from a squash line of interest using tissue from a the plant. The cells or protoplasts are generally provided by leaf, pollen, cotyledon, hypocotyl, embryos, root, fruit, flower, seed, shoot or stem tissue. The skilled breeder will recognize that various techniques may be employed for transforming squash. A commonly used technique is through regenerating squash from tissue culture, for instance protoplasts or regenerable cells transformed to contain one or more transgenes operably linked to regulatory elements functional in the squash plant.

"Resistant" or "resistance" is the preferred term in describing a plant, line or cultivar that shows fewer or reduced symptoms to a biotic pest or pathogen than a susceptible plant, line or variety to that biotic pest or pathogen. Tolerance is more often used to describe a response to abiotic or environmental influences (ozone, pollution, herbicide application, etc.). The literature is somewhat imprecise in the use of the terms "resistant" or "tolerant," however, with both terms variously applied to describe plants that show no symptoms as well as plants showing some symptoms but that are still able to produce marketable product with an acceptable yield. Some lines that are referred to as resistant or tolerant are only so in the sense that they may still produce a crop, even though the plants are stunted and the yield is reduced.

The International Seed Federation (ISF) is a non-governmental, non-profit organization representing the seed industry. According to the "ISF Definition of the Terms Describing the Reaction of Plants to Pests or Pathogens and to Abiotic Stresses for the Vegetable Seed Industry" (May 2005), the recognition of whether a plant is subject to a pest or pathogen can depend on the analytical method employed. The ISF definition for immunity is a plant that is "not subject to attack or infection by a specified pest or pathogen."

Resistance is defined by the ISF as the "ability of a plant types to restrict the growth and development of a specified pest or pathogen and/or the damage they cause when compared to susceptible plant varieties under similar environmental conditions and pest or pathogen pressure."

Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure.

Susceptibility is defined as the inability of a plant variety to restrict the growth and development of a specified pest or pathogen. For purposes of squash plants, a plant, line or cultivar, is "susceptible" where the plant, line or cultivar shows severe symptoms of infection by the virus, typically resulting in plant stunting, lower yields and a deformed or discolored crop.

Tests for rating viral resistance are variable, and many of the tests adapted by breeders and pathologists for the greenhouse being particularly severe. These tests tend to use a viral challenge with a high titer and to challenge plants at the most susceptible developmental stage. As such, the viral test results for greenhouse trials often indicate lower levels of resistance than are observed in the field under natural disease pressure.

Because tests for determining resistance levels are so varied, with results differing depending on the nature of the test, a standardized protocol was been adopted for evaluating the resistance of the squash lines described. For purposes of this disclosure, then, the terms "resistant" and "resistance" are applied to squash lines or cultivars, rather than individual plants. Individual plants are inoculated and evaluated using the methods described in the examples below. Each plant is given a resistance score on a scale of 1 to 5, based on the severity of the reaction or symptoms, with 1 being the resistance score applied to plants having no symptoms, and 5 the score applied to the plants with the most severe symptoms.

A line is rated as being resistant when at least 75% of the plants have a resistance score at a 1, 2 or 3 level, meaning less than 25% of the plants have the most severe symptoms of a score of 4 or 5. Susceptible lines are those that have more than 25% of the plants scoring at a 4 or 5 reaction level.

A high resistance rated line will have at least 75% of the plants score at a 1 or 2 level. An intermediate resistance line rated is one that is resistant, but does not rate at the high resistance level based on the resistance scores.

Alternative protocols for rating the level of resistance of lines to viruses are known in the art, and can also be used. A "high resistance" SLCV line will have an average resistance score of about 2.0 or less, when evaluated on a scale of 1 to 5, where the score is least 0.5 better than the average SLCV resistance score obtained from parent line, ZGY 46-2604 (Entry 1), when grown under comparable conditions.

Of the high resistance rated SLCV lines, line Entry 8 shows good characteristics as a parent for commercial green zucchini hybrids. This line has cylindrical fruit shape, uniform color, minimum branching, high resistance to geminivirus, intermediate resistance to potyvirus, and good immature fruit production. Entry 8 also shows resistance to combined infection of SLCV and potyviruses, at a level only slightly more susceptible than intermediate resistance (Table 3). This is important for practical purposes.

In many areas of squash cultivation there are multiple viruses present. For this reason, the addition of a commercial level of intermediate potyvirus resistance will be desired in some lines. There are additionally provided, then, squash lines with high resistance to geminivirus as well as intermediate resistance, as measured by the ZWP score, to potyviruses.

The ZWP test described below is a greenhouse test for potyvirus resistance that is much more severe than any likely field condition. Squash plants are simultaneously challenged with a high titer of a mixture of all three of the common squash potyviruses, at the most sensitive early stage of growth.

The results show that geminivirus resistance can be elevated by the process of breeding for combined geminivirus and potyvirus resistance traits. The converse does not appear to be true from these same results. So far, the best selections for SLCV resistance (or combined SLCV and potyvirus resistance?) have a lower potyvirus resistance than the potyvirus resistant donor parent.

Potyvirus resistance is multigenic and difficult to maintain without continuous selection pressure during subsequent generations. During the breeding process, selection for potyvirus resistance was done in early generations, but ultimately breeding lines represented in Entries 6-9 failed to recover the optimal set of alleles for potyvirus resistance, due to the many other selection criteria that were also involved (e.g. geminivirus resistance, horticultural characteristics, marketable fruit). Larger populations and/or backcross(es) would be expected to achieve higher potyvirus resistance, and the skilled breeder will recognize that potyvirus resistance levels as high as the donor parent could be achieved through additional generations of breeding and selection.

In any case, the potyvirus resistance observed for the high resistance geminivirus squash lines is commercially valuable. There are many commercial hybrids with resistance to potyvirus on the market, but very few with the level of resistance exemplified by Entry 5 (Table 2, below). Non-transgenic potyvirus resistance is polygenic, largely recessive, and some of the genes are specific to individual potyviruses, while others are not. As a result, it has proven quite difficult for breeders to develop varieties with the highest level of resistance to potyviruses (which are available in some wild or semi-domesticated relatives) which also retain the fruit and plant characteristics preferred by commercial growers. As evidence, compare the level of resistance shown by Entry 5 (Table 2, below) to the commercial variety Contender, which is widely regarded to have one of the better levels of potyvirus resistance available in the marketplace today. The main cultivars on the market today claiming resistance to potyvirus are hybrids such as Dividend, Payroll, Revenue, Contender, and Noche (Rogers, green zucchinis); Tigress, Prestige, and Lynx (Harris Moran, green zucchinis); Lioness (Harris Moran, yellow straightneck); Otto (Syngenta, Lebanese type). Seminis presently has five nontransgenic commercial squash hybrids with potyvirus resistance: Sungreen and Quirinal (green zucchinis), Terminator (gray zucchini), Revera and Marzouka (Lebanese).

It is seen from the results shown in the tables that each of Entry 5 through Entry 9 provide a level of ZWP resistance that is better than what is available in the non-transgenic commercial prior art lines that are reported as having potyvirus resistance. Lioness and Contender are the two prior art squash hybrids that are reported as having potyvirus resistance in the experiment described in the experiments. Conqueror III is a transgenic virus resistant squash hybrid that showed the highest level of potyvirus resistance in the experiments.

Thus, while the levels of resistance seen against SLCV for line Entries 6 through 9 is not duplicated under the severe conditions of the ZWP test for potyvirus resistance, Entries 6, 8, and 9 have an intermediate resistance rating. In this regard, Entries 6, 8, and 9 also show a higher level of potyvirus resistance than Contender and Lioness in the ZWP test. Though not all of the potyvirus resistance present in Entry 5 was recovered in Entries 6 through 9, what was recovered in Entries 6 and 9 still represents a level of potyvirus resistance higher than the nontransgenic commercial prior art, as shown in Entries 2, 4 and 10 (Contender, a breeding line derived from Tigress, and Lioness). Intermediate resistance under the conditions of the ZWP test will provide a highly valuable level of resistance for a squash line against potyviruses under normal field conditions.

The results thus demonstrate that resistance to geminivirus can be boosted and high level resistance to SLCV attained by crossing intermediate resistance geminivirus lines to potyvirus resistance lines. It is also possible to maintain intermediate potyvirus resistance in progeny lines by selection.

EXAMPLES

Example 1

Viral Screens for Potyviruses

The ZYMV, WMV-2, and PRSV potyviruses were originally isolated from infected cucurbit plants collected in California by Seminis scientists. Each virus was maintained separately in a susceptible squash line, via mechanical transferring once every 8 to 10 weeks in an insect-proof greenhouse. For virus inoculation, squash seed were germinated in the Sunshine Mix (Sun-Grow Horticulture, 18827 Willamette Dr., West Linn, Oreg. 97008) and grown in greenhouse at 18 to 24 degree C. until the cotyledons were fully expanded.

The inoculum was prepared by homogenizing with a blender 1 g of leaf tissues infected with each virus (ZYMV, WMV-2, and PRSV) in 50 ml of cold phosphate buffer (0.1 M) at pH 7.0 (5.3 g of $KH_2PO_4$ and 14.0 g of $K_2HPO_4 3H_2O$ in 1 liter of $H_2O$ and the pH adjusted with 1M of KOH solution).

The cotyledons were dusted with diatomaceous earth, rubbed with cheesecloth that had been soaked in the inoculum and then rinsed with water. The source of diatomaceous earth: Dicalite, Dicalite Minerals Corp. 225 City Ave., Suite 14, Bala Cynwyd, Pa. 19004.

Symptom evaluations for potyvirus are performed five to six weeks after inoculation. Symptoms are evaluated on a scale of 1 to 5, designated the "ZWP score".

A reaction designated a (5) on this scale is characterized in that following infection, all the leaves show severe distortion and plants are severely stunted with short internodes and narrowing and split leaf blade. The plants usually do not reach mature stage and may die in severe cases.

A ZWP score (4) means that all the leaves are severely distorted at all growing stages of the plant. The distortion is manifested as mottling, blistering, leaf blade narrowing and irregular splitting. The plants are severely stunted and may survive and produce distorted and unmarketable fruits.

The ZWP score (3) is characterized in that the first few true leaves show mild distortion with moderate mottling but no leaf narrowing nor splitting. As the plants grow older, the foliar symptoms may become milder and the plant may reach full size and produce either normal fruits or fruits with mild mottling and distortion.

In a ZWP score (2), plants characteristically show only a few chlorotic spots on the older leaves at young age. The youngest leaf is typically free of any symptoms. As the plants grow older the symptoms on the older leaves could also disappear and the plants may produce normal fruits that are free of symptoms.

In the Zwp score of (1) plants are free of any apparent symptoms at the time of reading (and generally throughout the entire life cycle).

Example 2

Viral Screens for Geminiviruses

The SLCV used in the inoculation was obtained from the virology department at the USDA-ARS at Salinas, Calif. The strain of SLCV was originally isolated from an infected squash plant collected near the Imperial Valley, Calif. The strain was maintained in squash variety Grey Zucchini via mechanical transferring once every 6 to 8 weeks in a greenhouse that excluded insects such as aphids and whitefly. SLCV can also be obtained from the USDA. The USDA source of SLCV is Dr. Hsing-Yeh Liu, USDA-ARS, 1636, E. Alisal St. Salinas, Calif. 93905.

Those skilled in the art will also recognize that they can obtain this virus from the field and maintain it according to the methods described below.

For virus inoculation, squash seeds were germinated in the Sunshine Mix and grown in the greenhouse at 18 to 24 degree C. until the first true leaf reached 2 cm diameter. The inoculum was prepared by homogenizing with a blender 1 g of infected tissues in 25 ml of cold potassium phosphate buffer (0.1 M) at pH 8.0.

Seedlings were spray-inoculated at approximately 30 cm from the tip of the nozzle with a sprayer (Syphon™ Gun, model 79SG012, by Guardair, WWW.labsafety.com) at 90-100 psi with the inoculum mixed with 7% diatomaceous earth and then rinsed with water.

The plants were inoculated the second time one week after the first inoculation. The symptoms were evaluated 3 to 4 weeks after the second inoculation.

Symptoms are evaluated on a 1 to 5 scale, designated the "SLCV score". The most severe reaction is designated a (5) on this scale, and is characterized in that following infection newly developing leaves are curled, with bright yellow mosaic. Yellow patterns on leaves are concentrated around leaf margins in some genotypes. Successive leaves are similar, but smaller, leading to a rosette type habit around the growing tip(s) of the plant. Stunting develops rapidly, and will usually lead to necrosis of all growing tips. Infected plants sometimes produce a profusion of flowers, many of which do not open or do not open normally, often with highly reduced petals. The plant dies before fruiting.

A SLCV score (4) means that the youngest leaf shows many spots and is curled under and older leaves show severe mottling and distortion, but the plant may survive to produce some poorly developed and misshapen fruit.

The SLCV score (3) is characterized in that following infection, the youngest leaf shows a small spot or two and is often curled under and the older leaves had obvious mottling and distortion, with a diffuse yellow mosaic. Successive leaves beyond the first which shows symptoms show decreasing symptoms and in the weeks following symptom development the normal growth habit returns to the plant. New leaves, 5 or more leaves after initial symptom development, show very mild mosaic, but not curling. Late in the life cycle of the plant, when pollinated fruit are approaching physiological maturity, new leaves may once again show intermediate mosaic and mild curling. Reduction of petals on flowers may be exhibited, but this symptom is also transient.

SLCV score (2) means that some spotting appeared on the older leaves (those first showing symptoms described above) but not on the youngest leaves, as described for SLCV resistant score (3). Rather than 5 or more nodes before the disappearance of symptoms, in a (2) reaction symptoms disappear between the second and fourth leaf following symptom display. Fruit production is acceptable, with only mild discoloration.

In the SLCV reaction (1), following infection a single newly developing leaf may show mild mosaic, but no curling. Successive leaves show no apparent symptoms of virus infection. Reduction of petals is not observed. Fruit yield of the plants is generally unaffected.

Example 3

Viral Screens for Combined Potyviruses and Geminiviruses

Squash seed were germinated and grown as described above until the cotyledons were fully expanded. The seedlings were inoculated with the ZYMV, WMV-2, and PRSV potyviruses as described above.

Approximately one week later when the first true leaf reached a 2 cm diameter, the seedlings were inoculated with SCLV the same way described above. The plants were inoculated the second time with SCLV one week after the first SCLV inoculation. The symptoms were evaluated 3 to 4 weeks after the second SCLV inoculation.

A rating system like that described above was used to evaluate the resistance to infection with all four viruses. Symptoms are evaluated on a 1 to 5 scale, designated the "Combined score". The most severe reaction is designated a (5) and may show severe symptoms characteristic of either the ZWP or SLCV score, or some combination of these severest symptoms. This is because a plant my be susceptible to all, some, one or none of the viruses.

Similarly, a score (4) means would correspond to level 4 symptoms characteristic of either the ZWP or SLCV score, or some combination of these symptoms, and likewise for a Combined score (3) and Combined score (2). A combined score (1), as for the ZWP and SLCV scores, means that following infection a single newly developing leaf may show only the mildest symptoms, while successive leaves show no apparent symptoms of virus infection.

Example 4

Potyvirus Resistant Parent Development

The advanced line HP13HMW/HP134*1 (Entry 5) was developed as follows. HMW is a squash breeding line with a highly branching growth habit and fruit having an odd coloration pattern (spotted or "smudgy" appearance). The fruit has a prominent constriction near the stem end, and that the line has severe fertility problems and sets very few seeds per fruit. This line was received by Seminis as an accession from Cornell University in the early and mid 1980s, among a large group of squash accessions which were segregating for resistance to potyviruses.

HMW was among a group of accessions crossed to a Seminis parent line HP13, female parent of a commercial hybrid, in order to develop breeding materials with both a high level of potyvirus resistance and commercially acceptable fruit type. In the F2 generation hundreds of seedlings were inoculated with a cocktail of viruses including ZYMV, WMV-2, and PRSV, as described in example 1. Surviving seedlings from this inoculation were moved to a greenhouse, where individual F2 plants exhibiting reduced branching, improved dark green fruit color, and less constriction on fruits were selected for self pollination. At the time of seed maturity, the subset of selections with improved seed yield (compared to the HMW donor parent) was chosen for experiments in the F3 generation. This process was repeated for several generations in the mid 1980s, and HP13HMW was selected as the final product parent line of this first cross, because it had improved plant and fruit characters (compared to HMW) and retained the high level potyvirus resistance.

HP13HMW was then crossed to HP134, the female of a different, newer commercial hybrid, chosen as the recurrent parent because it exhibited a better plant and fruit type than HP13, which had been the best parent line available at that time. In the F2 generation seedlings were inoculated with a cocktail of viruses including ZYMV, WMV-2, and PRSV. Individual F2 plants exhibiting few or no viral symptoms after two weeks were transplanted to fields, where plants with reduced branching, improved dark green fruit color, and less constriction on fruits were selected for self pollination. This process was repeated with generations alternating in California (summer) and Florida (winter). Several advanced progeny lines (F5 and later) derived from this cross were then used for progeny testing. Progeny tests involve crossing the entire group of potential new parent lines to a group of alternate parent lines, followed by evaluation of the performance of the new parent lines through replicated tests of the hybrids. Hybrids were evaluated in California, Florida, Italy, and other locations with commercial growers. The best potential new parent line was self pollinated, selected to the F8 generation, and designated ZGN 47-5012.

ZGN 47-5012 thus has pedigree HP13HMW/HP134, but still had not recovered all of the fruit quality traits needed in certain markets. Specifically, this parent line did not provide hybrids with a dark green color intensity sufficient for the winter production cycles in Mexico, where stronger color intensity was needed to combat the color loss due to silvering disease (from intense pressure of *Bemisia argentifolii* populations). HP13HMW/HP134 was therefore again backcrossed to HP134, the potyvirus susceptible recurrent parent, in 1996, and an additional cycle of parental line development was initiated. In the F2 generation hundreds of seedlings were inoculated with a cocktail of viruses including ZYMV, WMV-2, and PRSV. Individual F2 plants exhibiting few or no viral symptoms after two weeks were transplanted to fields. This process was repeated with generations alternating in California (summer) and Florida (winter). In the field plants exhibiting the best fruit quality and earliness were selected for self pollination. After the F6 generation, a single line was advanced without further selection. This breeding line (Entry 5, Table 1, 2, 3)), is designated as HP13HMW/HP134*1, reflecting the pedigree. Entry 5 was included as a parent in a battery of progeny tests along with ZGN 47-5012, and the resultant hybrids were evaluated in multiple trials in California, Florida, and Sinaloa, as well as in virus screens to verify a high level of potyvirus resistance. Entry 5 proved to have excellent fruit quality and the same level of potyvirus resistance as ZGN 47-5012. Entry 5 did not meet certain other desired horticultural requirements, and was not further developed for use as the parent of a commercial variety. Its use as a source of germplasm for additional breeding was continued (see below). Line ZGN 47-5012 is a closely related selection to Entry 5, having the same resistance to potyvirus, but with additional desired horticultural traits.

There are other sources of potyvirus resistance, including Tigress, a hybrid from Harris Moran Seed Company. Tigress was the first commercial hybrid squash claiming resistance to multiple potyviruses. An advanced selection of Tigress is represented by ZGN 130-1003 in Table 1 (Entry 4). This line was developed by self pollinating the commercial hybrid, followed by repeated generations of selection for resistance to potyviruses and for acceptable fruit and plant type. In the F2 generation seedlings were inoculated with a cocktail of viruses including ZYMV and WMV-2. Individual F2 plants exhibiting few or no viral symptoms after two weeks were transplanted to fields. In the field, plants with improved dark green fruit color were selected for self pollination. This selection process was repeated, alternating generations between California (summer) and Florida (winter). Replicated progeny testing of hybrids from advanced lines in Florida, California, Sonora, and Sinaloa led to the selection of the parent line designated ZGN 130-1003. The parent line derived from the cultivar Tigress has good fruit quality, but the level of potyvirus resistance in this parent line is much lower than in Entry 5 or line ZGN 47-5012.

Example 5

High Level Geminivirus Resistant Green Zucchini Squash Lines

The breeding lines with genotype (ZGN130-1003/(ZGY46-2604/G710*1F6))/(HP13HMW/HP134*1) described in this experiment were developed by a complex selection strategy. There are four components to the genotype:

ZGN 130-1003—a proprietary Seminis breeding line contributing fruit quality characteristics and some potyvirus resistance (Entry 4, described in example 4);

ZGY 46-2604—the original gray zucchini source of resistance to SLCV from Sergio Garza (Entry 1);

G710—a proprietary Seminis breeding line contributing fruit quality characteristics; and HP13HMW/HP134*1—a proprietary Seminis breeding line contributing high resistance to ZYMV, WMV-2, and PRSV (Entry 5, example 4).

ZGY 46-2604 was crossed to a series of proprietary breeding lines including G710 immediately after receiving this SLCV resistance accession, in order to develop breeding populations with a combination of SLCV resistance and acceptable fruit types in a variety of market classes. The resulting F1 progeny of this cross was backcrossed to G710, and the BC1F2, BC1F3, and BC1F4 generations were selected for fruit and plant characteristics without regard to SLCV virus resistance in Tifton, Ga.

The self-pollinated BC1F5 progeny selections were included in a field trial in the Rio Grande Valley of Texas in late summer 2000 (a location and date chosen for its history of SLCV epidemics). Heavy SLCV pressure allowed the tentative identification of breeding lines with SLCV resistance, but the observations were confounded by high levels of potyvirus infestation in the same field. Nineteen selections (or remnant seed in the case of failed pollinations) were chosen to be planted in the greenhouse at Woodland, Calif. in February, 2001 and inoculated with SLCV (Example 2). Four BC1F5 and BC1F6 families were selected for a high level of resistance to SLCV and for fruit quality characteristics which best matched green zucchini market characteristics.

The selected families were crossed to a series of 31 Seminis proprietary breeding lines in the spring of 2001. During the summer of 2001, these proprietary breeding lines were evaluated for virus resistance (through individual and cocktail screens of potyviruses) and for fruit quality characteristics in Woodland Calif. Ten hybrids were selected, and these ten hybrids were subsequently evaluated for resistance to SLCV in a nursery planted in Hermosillo, Mexico in late 2001. In the critical step of the development of the population, one hybrid (ZGN130-1003/(ZGY46-2604/G710*1)) was selected for development of new germplasm. This hybrid was planted in the greenhouse at Woodland Calif. in February 2002, and was crossed to line HP13HMW/HP134*1 (Entry 5, chosen for high level potyvirus resistance and good fruit characteristics).

The resulting F1 population known as (ZGN130-1003/(ZGY46-2604/G710*1F6))/(HP13HMW/HP134*1) was inoculated with a cocktail of ZYMV, WMV-2, and PRSV, and survivors were moved to the field in Woodland, Calif. in the summer of 2002. 37 individuals were selected from this population based on potyvirus resistance and fruit and plant characteristics. The F2 generations from these selections were sown in the greenhouse at Woodland Calif. in January 2003, and inoculated with ZYMV, WMV-2, PRSV, and SLCV.

The unexpected results of high SLCV resistance described here were first observed in this early 2003 screen, where F2 individuals in certain families showed much higher levels of resistance to SLCV than the original source of resistance, ZGY 46-2604 (Entry 1). These F2 individuals were self-pollinated.

F3 families derived from the F2 individuals with unexpectedly high levels of SLCV resistance were inoculated with a cocktail of ZYMV, WMV-2, and PRSV, and resistant individuals were transplanted to a field near Woodland Calif. in the summer of 2003. 102 F3 individuals were selected for self-pollination from this field based on their level of potyvirus resistance, and fruit and plant characteristics. Successful pollinations from the California F3 generation were sown in Florida (to evaluate fruit quality) and Sinaloa (for a simultaneous observation under heavy potyvirus and geminivirus natural pressure), and ten F4 families were selected. The field trial in Sinaloa allowed verification of the high level geminivirus resistance in an environment very similar to a commercial field. The selected lines provided a verification of the unexpected results from the early 2003 greenhouse screen, because the F4 generation also showed a higher level of resistance to natural geminivirus infection than the genotype which was the original source of resistance.

Not all of the self-pollinations were successful in the F4 generation, so some were recovered using remnant F4 seed in the first Woodland greenhouse cycle in January, 2004. Both F4 and F5 families were included, as available, in this early 2004 cycle, where selections were made following inoculation with SLCV. Again, these breeding lines demonstrated a higher level of resistance to geminivirus than the original source of resistance. Self pollination of these selections from the first greenhouse cycle of 2004 provided the F5 and F6 generation seeds used in the present experiment. The four families described in the Table 1 (designated as Entries 6-9) show uniform, high resistance to SLCV. Each of Entries 6 through 9 have the pedigree (ZGN130-1003/(ZGY46-2604/G710*1F6))/(HP13HMW/HP134*1). These four entries are separate lineages from the F1 generation.

Example 6

Evaluating Squash Lines for Enhanced Resistance

Lines developed as described above in Examples 4 and 5 were subjected to the SLCV and ZWP testing as described for Examples 1, 2 and 3.

Table 1 below provides the results of the SLCV testing.

TABLE 1

| Entry | Source/Hybrid | Generation | 1 | 2 | 3 | 4 | 5 | Total # of Plants | % 1 and 2 | % 1, 2 and 3 | % 4 and 5 | Ave. Score |
|---|---|---|---|---|---|---|---|---|---|---|---|---|
| 1 | ZGY 46-2604 | ADV | 2 | 36 | 18 | 3 | 1 | 60 | 63.33 | 93.33 | 6.67 | 2.42 |
| 2 | Contender | F1 | 0 | 7 | 26 | 39 | 0 | 72 | 9.72 | 45.83 | 54.17 | 3.44 |
| 3 | Grey Zucchini | OP | 1 | 1 | 3 | 58 | 9 | 72 | 2.78 | 6.94 | 93.06 | 4.01 |
| 4 | ZGN 130-1003 | ADV | 0 | 0 | 19 | 51 | 0 | 70 | 0.00 | 27.14 | 72.86 | 3.73 |
| 5 | Entry 5 | ADV | 2 | 3 | 15 | 53 | 0 | 73 | 6.85 | 27.40 | 72.60 | 3.63 |
| 6 | Entry 6 | F5 | 29 | 41 | 0 | 0 | 1 | 71 | 98.59 | 98.59 | 1.41 | 1.63 |
| 7 | Entry 7 | F5 | 44 | 17 | 0 | 1 | 6 | 68 | 89.71 | 89.71 | 10.29 | 1.65 |
| 8 | Entry 8 | F6 | 18 | 53 | 0 | 0 | 0 | 71 | 100.00 | 100.00 | 0.00 | 1.75 |
| 9 | Entry 9 | F6 | 42 | 25 | 1 | 0 | 4 | 72 | 93.06 | 94.44 | 5.56 | 1.60 |
| 10 | Lioness | F1 | 0 | 2 | 21 | 38 | 3 | 64 | 3.13 | 35.94 | 64.06 | 3.66 |
| 11 | Conqueror III | F1 | 2 | 0 | 1 | 66 | 3 | 72 | 2.78 | 4.17 | 95.83 | 3.94 |

Table 2 below provides the results of the testing using the ZWP test.

TABLE 2

| Entry | Source/Hybrid | Generation | 1 | 2 | 3 | 4 | 5 | Total # of Plants | % 1 and 2 | % 1, 2 and 3 | % 4 and 5 | Ave. Score |
|---|---|---|---|---|---|---|---|---|---|---|---|---|
| 1 | ZGY 46-2604 | ADV | 0 | 0 | 0 | 66 | 2 | 68 | 0.00 | 0.00 | 100.00 | 4.03 |
| 2 | Contender | F1 | 0 | 0 | 0 | 72 | 0 | 72 | 0.00 | 0.00 | 100.00 | 4.00 |
| 3 | Grey Zucchini | OP | 0 | 0 | 0 | 72 | 0 | 72 | 0.00 | 0.00 | 100.00 | 4.00 |
| 4 | ZGN 130-1003 | ADV | 0 | 1 | 53 | 12 | 0 | 66 | 1.52 | 81.82 | 18.18 | 3.17 |
| 5 | Entry 5 | ADV | 0 | 47 | 18 | 0 | 0 | 65 | 72.31 | 100.00 | 0.00 | 2.28 |
| 6 | Entry 6 | F5 | 0 | 10 | 45 | 7 | 0 | 62 | 16.13 | 88.71 | 11.29 | 2.95 |
| 7 | Entry 7 | F5 | 0 | 0 | 5 | 62 | 2 | 69 | 0.00 | 7.25 | 92.75 | 3.96 |
| 8 | Entry 8 | F6 | 0 | 0 | 55 | 14 | 0 | 69 | 0.00 | 79.71 | 20.29 | 3.20 |
| 9 | Entry 9 | F6 | 0 | 9 | 48 | 7 | 0 | 64 | 14.06 | 89.06 | 10.94 | 2.97 |
| 10 | Lioness | F1 | 0 | 0 | 12 | 46 | 8 | 66 | 0.00 | 18.18 | 81.82 | 3.94 |
| 11 | Conqueror III | F1 | 1 | 57 | 8 | 1 | 0 | 67 | 86.57 | 98.51 | 1.49 | 2.13 |

Table 3 below provides the results of the combined ZWP and SLCV testing.

TABLE 3

| Entry | Source/Hybrid | Generation | 1 | 2 | 3 | 4 | 5 | Total # of Plants | % 1 and 2 | % 1, 2 and 3 | % 4 and 5 | Ave. Score |
|---|---|---|---|---|---|---|---|---|---|---|---|---|
| 1 | ZGY 46-2604 | ADV | 0 | 0 | 0 | 65 | 3 | 68 | 0.00 | 0.00 | 100.00 | 4.04 |
| 2 | Contender | F1 | 0 | 0 | 0 | 71 | 0 | 71 | 0.00 | 0.00 | 100.00 | 4.00 |
| 3 | Grey Zucchini | OP | 0 | 0 | 0 | 60 | 11 | 71 | 0.00 | 0.00 | 100.00 | 4.15 |
| 4 | ZGN 130-1003 | ADV | 0 | 0 | 0 | 56 | 6 | 62 | 0.00 | 0.00 | 100.00 | 4.10 |
| 5 | Entry 5 | ADV | 0 | 5 | 4 | 61 | 1 | 71 | 7.04 | 12.68 | 87.32 | 3.82 |
| 6 | Entry 6 | F5 | 0 | 17 | 30 | 17 | 7 | 71 | 23.94 | 66.20 | 33.80 | 3.20 |
| 7 | Entry 7 | F5 | 0 | 11 | 24 | 26 | 10 | 71 | 15.49 | 49.30 | 50.70 | 3.49 |
| 8 | Entry 8 | F6 | 0 | 23 | 28 | 19 | 0 | 70 | 32.86 | 72.86 | 27.14 | 2.94 |
| 9 | Entry 9 | F6 | 0 | 27 | 32 | 10 | 3 | 72 | 37.50 | 81.94 | 18.06 | 2.85 |
| 10 | Lioness | F1 | 0 | 0 | 2 | 65 | 1 | 68 | 0.00 | 2.94 | 97.06 | 3.99 |
| 11 | Conqueror III | F1 | 0 | 6 | 0 | 64 | 0 | 70 | 8.57 | 8.57 | 91.43 | 3.83 |

Example 7

Hybrid Seed Production

To produce hybrid squash seed highly resistant to geminivirus, inbred lines having high resistance to geminivirus are crossed with plants having desirable fruit quality and agronomic traits.

Hybrids have been produced having as one parent high resistance geminivirus lines, and the patterns of enhanced geminivirus resistance have been observed in the hybrids.

For hybrid seed having intermediate potyvirus resistance in combination with high resistance to geminivirus, squash lines with geminivirus and potyvirus resistance are crossed to squash lines having potyvirus resistance. Resulting hybrids have intermediate potyvirus resistance and high resistance to geminivirus.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

Deposit Information

A deposit has been made of the Seminis Vegetable Seeds, Inc. proprietary inbred line Entry 8, disclosed above, with the American Type Culture Collection (ATCC), Manassas, Va. 20110-2209 USA, an International Depositary Authority (IDA) as established under the Budapest Treaty on the International Recognition of the Deposit of Micro-organisms for the Purposes of Patent Procedure. The accession number for line Entry 8 is ATCC Deposit No. PTA-6962.

A deposit has also been made with the ATCC of the Seminis Vegetable Seeds, Inc. proprietary inbred lines ZGN 47-5012 and Entry 1, disclosed above. The accession number for line ZGN 47-5012 is ATCC Deposit No. PTA-6960. The accession number for line Entry 1 is ATCC Deposit No. PTA-6961.

Upon issuance of a patent, all restrictions upon the deposits will be removed, and the deposits are intended to meet all of the requirements of 37 C.F.R. §1.801-1.809.

What is claimed is:

1. A squash plant or a part thereof having high resistance to geminivirus, wherein said squash plant, or a part thereof, shares a genetic source with a squash line selected from the group consisting of line Entry 1, having seed deposited with the ATCC under ATCC Accession No. PTA-6961; line Entry 8, having seed deposited with the ATCC under ATCC Accession No. PTA-6962; line entry ZGN 47-5012, having seed deposited with the ATCC under ATCC Accession No. PTA-6960.

2. The squash plant or a part thereof of claim 1, having intermediate resistance to potyvirus.

3. The squash plant or a part thereof of claim 1, wherein the plant is derived from the line HMW.

4. The squash plant or a part thereof of claim 1, with high resistance to SLCV.

5. The squash plant or a part thereof of claim 4, wherein greater than about 90% of scored plants have an SLCV resistance score of 1 or 2.

6. The squash plant or a part thereof of claim 1, wherein the plant is a summer squash.

7. The squash plant or a part thereof of claim 6, having yellow fruit.

8. The squash plant or a part thereof of claim 6, having cylindrical and substantially non-tapering fruit.

9. The squash plant or a part thereof of claim 1, wherein said part is a squash fruit or a seed of said squash plant and wherein a plant grown from said seed has high resistance to geminivirus.

10. The squash plant or a part thereof of claim 2, wherein said part is a squash fruit or a seed of said squash plant and wherein a plant grown from said seed has high resistance to geminivirus.

11. The squash plant or a part thereof of claim 3, wherein said part is a squash fruit or a seed of said squash plant and wherein a plant grown from said seed has high resistance to geminivirus.

12. The squash plant or a part thereof of claim 4, wherein said part is a squash fruit or a seed of said squash plant and wherein a plant grown from said seed has high resistance to geminivirus.

13. The squash plant or a part thereof of claim 1, wherein said squash plant or a part is not transgenic.

* * * * *